(12) United States Patent
Furuta et al.

(10) Patent No.: US 9,046,456 B2
(45) Date of Patent: Jun. 2, 2015

(54) INDENTATION TESTER

(71) Applicant: MITUTOYO CORPORATION, Kanagawa (JP)

(72) Inventors: Eiji Furuta, Sagamihara (JP); Takeshi Sawa, Kawasaki (JP)

(73) Assignee: MITUTOYO CORPORATION, Kanagawa (JP)

( * ) Notice: Subject to any disclaimer, the term of this patent is extended or adjusted under 35 U.S.C. 154(b) by 259 days.

(21) Appl. No.: 13/893,481

(22) Filed: May 14, 2013

(65) Prior Publication Data
US 2013/0319091 A1 Dec. 5, 2013

(30) Foreign Application Priority Data

May 31, 2012 (JP) .................................. 2012-123893

(51) Int. Cl.
*G01N 3/44* (2006.01)
*G01N 3/42* (2006.01)

(52) U.S. Cl.
CPC .. *G01N 3/44* (2013.01); *G01N 3/42* (2013.01); *G01N 2203/021* (2013.01); *G01N 2203/0206* (2013.01)

(58) Field of Classification Search
CPC ............ G01N 3/42; G01N 2203/0082; G01N 2203/0206; G01N 2203/021; G01N 35/00594; G01N 35/00693; G01N 3/44
USPC .............................................................. 73/81
See application file for complete search history.

(56) References Cited

U.S. PATENT DOCUMENTS

| 4,435,976 | A | * | 3/1984 | Edward, Jr. ........................ 73/83 |
| 4,691,559 | A | * | 9/1987 | Fischer .............................. 73/81 |
| 4,841,764 | A | * | 6/1989 | Fischer .............................. 73/81 |
| 4,848,141 | A | * | 7/1989 | Oliver et al. ....................... 73/81 |
| 5,309,754 | A | * | 5/1994 | Ernst ................................. 73/81 |
| 6,142,010 | A | * | 11/2000 | Merck et al. ...................... 73/81 |
| 7,096,720 | B2 | * | 8/2006 | Hayashi et al. ................... 73/81 |
| 7,121,136 | B2 | * | 10/2006 | Tsujii et al. ....................... 73/81 |
| 7,302,831 | B2 | * | 12/2007 | Moyse et al. ..................... 73/81 |
| 8,074,497 | B2 | * | 12/2011 | Sawa et al. ....................... 73/81 |
| 8,087,282 | B2 | * | 1/2012 | Sawa et al. .................... 73/1.89 |
| 8,201,441 | B2 | * | 6/2012 | Handschuck et al. ........... 73/82 |
| 8,655,602 | B2 | * | 2/2014 | Sawa ............................. 702/42 |
| 8,833,138 | B2 | * | 9/2014 | Klein et al. ................. 73/12.13 |
| 8,849,588 | B2 | * | 9/2014 | Sawa et al. ..................... 702/41 |
| 2013/0047712 | A1 | | 2/2013 | Ariga et al. |

FOREIGN PATENT DOCUMENTS

JP    2009-156688 A    7/2009

* cited by examiner

*Primary Examiner* — Freddie Kirkland, III
(74) *Attorney, Agent, or Firm* — Greenblum & Bernstein, P.L.C.

(57) ABSTRACT

Indentation tester capable of adjusting vertical-direction positioning drift due to individual differences of an indenter when indenters are switched includes an adjustment mechanism. The adjustment mechanism adjusts relative vertical-direction positions of a displacement sensor movable portion and a displacement sensor fixed portion. The adjustment mechanism includes a first hollow disk having a spiraling surface formed on a bottom surface; and a second hollow disk having a spiraling surface formed on a top surface. The spiraling surface of the second hollow disk has a thread equal to that of the spiraling surface of the first hollow disk. The first hollow disk rests on the second hollow disk such that the bottom surface of the first hollow disk is overlaid on the top surface of the second hollow disk. The first hollow disk and the second hollow disk are capable of rotation on a center axis of an indenter column.

12 Claims, 9 Drawing Sheets

INDENTATION TESTER

CROSS-REFERENCE TO RELATED APPLICATIONS

The present application claims priority under 35 U.S.C. §119 of Japanese Application No. 2012-123893, filed on May 31, 2012, the disclosure of which is expressly incorporated by reference herein in its entirety.

BACKGROUND OF THE INVENTION

1. Field of the Invention

The present invention relates to an indentation tester.

2. Description of Related Art

Conventionally, a material tester is known in which an indentation tester forms an indentation by pressing an indenter column into a surface of a sample, the indenter column having an indenter on a foremost end thereof. The indentation tester then measures a depth of the indentation (displacement amount of the indenter) with a displacement gauge. Using a relationship between the displacement amount and a load placed on the indenter, the indentation tester measures values for physical characteristics of the sample, such as hardness. (See, for example, Japanese Patent Laid-open Publication No. 2009-156688.) Using the above-described indentation tester, a material testing method (instrumented indentation test) evaluates the indentation depth of a nanoindentation made by the indenter, for example. In this material testing method, in order to eliminate effects from elastic deformation of an indentation tester device body or sample holder, a measurement method using the sample surface as a baseline for the measurement of the indentation depth is effective.

However, due to the extremely high sensitivity of the device measuring the indentation depth, there is an exceptionally small margin for a baseline position. Simply by mounting a new indenter to the indenter column, a height of the indenter may vary due to individual differences in each indenter, leading to positioning drift in a vertical direction. Thus, when the indentation test is performed after switching indenters, there is a risk that measurement of a maximum indentation depth may not be performed to satisfaction or that resolution may be reduced. Therefore, in order that an indenter coupling (coupled to the indenter) is positioned at the vertical-direction baseline position for an indenter position detector (which measures the indentation depth) when the indenter reaches the sample surface, a mounting surface on the indenter or a contactor must be readjusted or a spacer must be inserted when switching indenters. The operation of switching indenters thus requires time and may also increase costs.

SUMMARY OF THE INVENTION

The present invention provides an indentation tester capable of readily and cheaply adjusting vertical-direction positioning drift due to individual differences of an indenter when indenters are switched.

One aspect of the present invention is an indentation tester including an indenter column, an indenter coupling, a load-applying mechanism, an indenter reference, an indenter position detector, a pressure brace, an indenter reference driver, and a measurer. The indenter column holds an indenter on a foremost end of the indenter column. The indenter coupling is affixed to the indenter column and couples with the indenter. The load-applying mechanism displaces the indenter column in an axis direction of the indenter column and applies a predetermined test force to a sample using the indenter. The indenter reference is a positioning reference for the foremost end of the indenter. The indenter position detector is coupled to the indenter reference and detects an amount of displacement of the indenter coupling. The pressure brace includes the indenter reference attached to a lower portion of the pressure brace and the indenter position detector on an upper portion of the pressure brace. The indenter reference driver displaces the indenter reference in the axis direction of the indenter column. The measurer displaces the indenter column in the axis direction while maintaining a state of contact between the indenter reference and a sample surface. The measurer then measures a depth of an indentation formed when the indenter, while in contact with the sample surface, was pressed against the sample. The indentation depth is measured by the indenter position detector detecting a displacement amount of the indenter coupling. The indentation tester further includes an adjustment mechanism adjusting a relative vertical-direction position relationship between the indenter coupling and the indenter position detector. The adjustment mechanism includes a first hollow disk and a second hollow disk. The first hollow disk includes a spiraling surface formed on a bottom surface. The second hollow disk includes a spiraling surface formed on a top surface, the spiraling surface of the second hollow disk having a thread equal to that of the spiraling surface of the first hollow disk. The first hollow disk rests on the second hollow disk such that the bottom surface of the first hollow disk is overlaid on the top surface of the second hollow disk. The first hollow disk and the second hollow disk are capable of rotation on a center axis of the indenter column.

Another aspect of the present invention is the indentation tester in which a platform on which the adjustment mechanism can be placed is formed near an outer circumferential surface of the indenter reference. In addition, a top surface of the first hollow disk is in contact with a bottom surface of the pressure brace and a bottom surface of the second hollow disk is in contact with the platform of the indenter reference.

Another aspect of the present invention is the indentation tester in which a platform on which the adjustment mechanism can be placed is formed near an outer circumferential surface of a portion of the indenter in contact with a bottom surface of the indenter column. In addition, a top surface of the first hollow disk is in contact with the bottom surface of the indenter column and a bottom surface of the second hollow disk is in contact with the platform of the indenter.

Another aspect of the present invention is the indentation tester in which one of the first hollow disk and the second hollow disk includes a guide portion guiding rotation of the other hollow disk.

Another aspect of the present invention is the indentation tester in which an outer circumferential surface of one of the first hollow disk and the second hollow disk includes a first indicator indicating a rotation-direction position of the hollow disk. In addition, the outer circumferential surface of the other hollow disk includes a second indicator indicating an amount of change in height of the adjustment mechanism.

The present invention enables adjustments to be readily made so as to position an indenter coupling at a vertical-direction baseline position of an indenter position detector when an indenter is positioned at a sample surface. In addition, the present invention enables adjustments to be readily and cheaply made to vertical-direction positioning drift that occurs when switching indenters due to individual differences in the indenter.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

Figure 1:
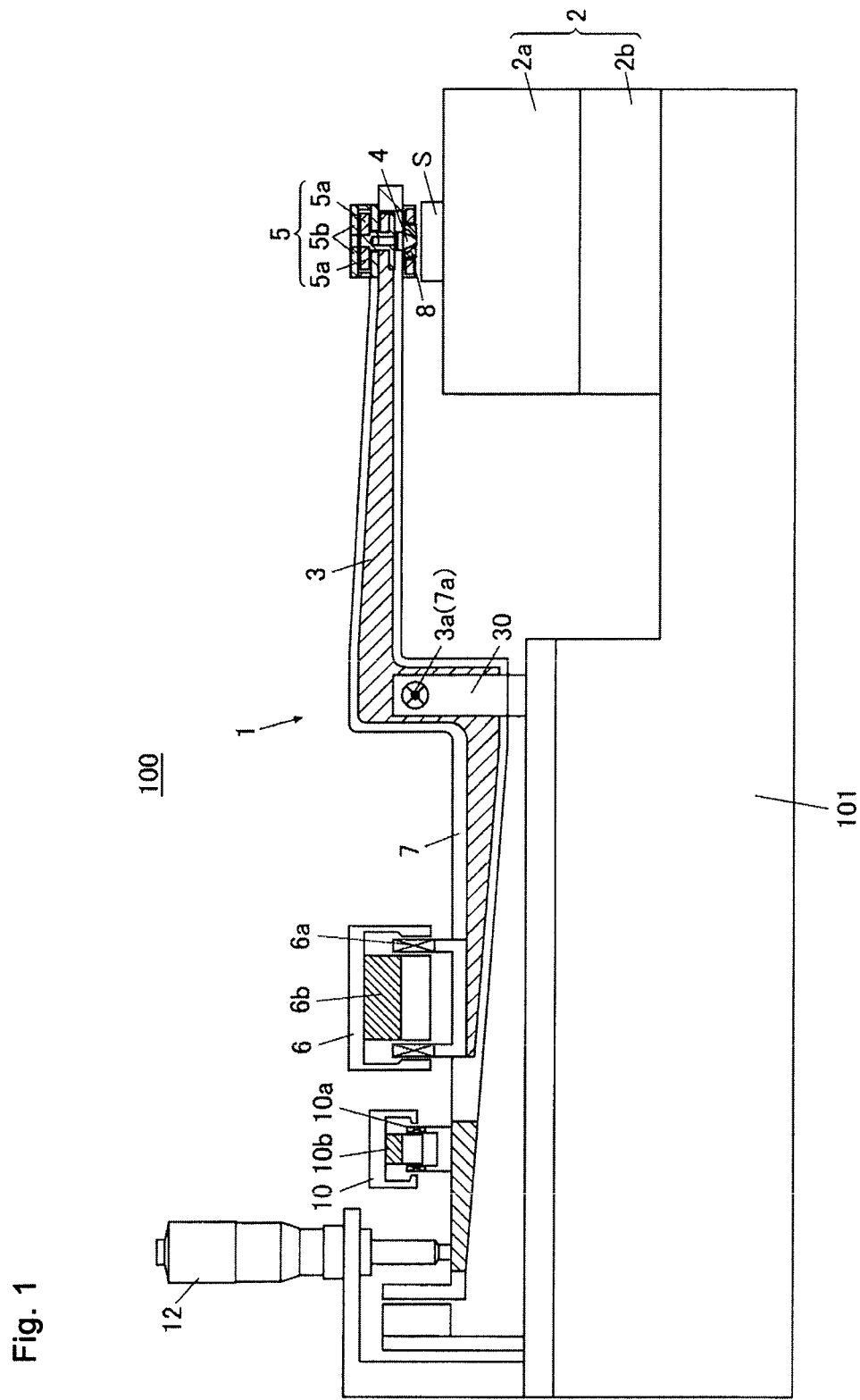
FIG. 1 is a side view in partial cross-section of an indentation tester according to a first embodiment of the present invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, embodiments of the present invention are described with reference to the drawings.

First Embodiment

An indentation tester 100 according to a first embodiment is a lever-type instrumented indentation tester capable of continuously monitoring a test force (load) applied to an indenter 4 and an indentation depth of the indenter 4.

As shown in FIGS. 1 to 5, the indentation tester 100 includes a tester main body 1 applying the test force to a sample S; a controller 200 controlling various components of the tester main body 1; a display 300; and an operator 400.

The tester main body 1 includes, for example: a stand 2 on which the sample S is placed; a load lever 3; an indenter column 41; a displacement sensor movable portion 5a (indenter coupling); a first force motor 6 (load-applying mechanism or load applier); a reference lever 7 (pressure brace); a contactor 8 (indenter reference); an adjustment mechanism (adjuster) 9; a displacement sensor fixed portion 5b (indenter position detector); a second force motor 10 (indenter reference driver); a stopper 12; and the controller 200 controlling various components of the tester main body 1. The load lever 3 is rotatably and axially supported on a support 30, which is provided to a base 101 of the indentation tester 100. The indenter column 41 holds an indenter 4 on a foremost end and is provided to a lower portion of a first end of the load lever 3. The displacement sensor movable portion 5a (indenter coupling) is provided to an upper portion of the first end of the load lever 3 and has an annular shape when viewed from above. The first force motor 6 (load-applying mechanism or load-applier) is provided to a second end of the load lever 3. The reference lever 7 (pressure brace) is rotatably and axially supported on the support 30. The contactor 8 (indenter reference) is detachably attached to a lower portion of a first end of the reference lever 7. The adjustment mechanism 9 is provided on an outer circumferential surface of the contactor 8. The displacement sensor fixed portion 5b (indenter position detector) is provided to an upper portion of the first end of the reference lever 7 and has an annular shape when viewed from above. The second force motor 10 (indenter reference driver) is provided to a second end of the reference lever 7. The stopper 12 makes contact with the second end of the reference lever 7.

The stand 2 is provided on a top surface of the base 101 and includes a sample holding stage 2a, on which the sample S is placed, and an XYZ stage 2b for adjusting a position of the sample S. The sample S is placed below the indenter 4 on the sample holding stage 2a such that the indenter 4 will press against the sample S when the load lever 3 is rotated. In addition, the sample S is supported on the sample holding stage 2a such that the sample S will not slip during testing and measurement. The XYZ stage 2b is configured to be displaceable in vertical, left-right, and front-back directions in accordance with a control signal input from the controller 200, enabling the XYZ stage 2b to adjust the position of the sample S resting on the sample holding stage 2a.

The load lever 3 is rotatably and axially supported on the support 30 by a rotation axis 3a, the support 30 being provided at substantially a center portion of the tester main body 1. The indenter 4 is provided to the lower portion of the first end of the load lever 3, with the indenter column 41 interposed between the indenter 4 and the load lever 3. In addition, the indenter 4 is affixed to the indenter column 41 by an indenter fixating screw 42 (see FIG. 3). The first force motor 6 is provided to the upper portion of the second end of the load lever 3.

The first force motor 6 includes, for example, a force coil 6a and a magnet 6b. Generated power is used as drive power, the power being generated in response to electric electromagnetic induction between a magnetic field created by the magnet 6b and an electric current flowing through the force coil 6a. The drive power causes the load lever 3 to rotate, thus pressing down or pressing up the first end of the load lever 3. The first end of the load lever 3 is pressed down with the drive from the first force motor 6, causing the indenter column 41 to displace in an axis direction of the indenter column 41. A load can thus be applied to the indenter 4 through the indenter column 41 to press the indenter 4 against the surface of the sample S. In other words, the first force motor 6 is a load-applying mechanism displacing the indenter column 41 in the axis direction to apply a predetermined test force on the sample S with the indenter 4.

The displacement sensor movable portion 5a is provided on the upper portion of the first end of the load lever 3. The displacement sensor movable portion 5a is vertically displaced in conjunction with the indenter 4, which is pressed up and down by the load lever 3.

Figure 2:
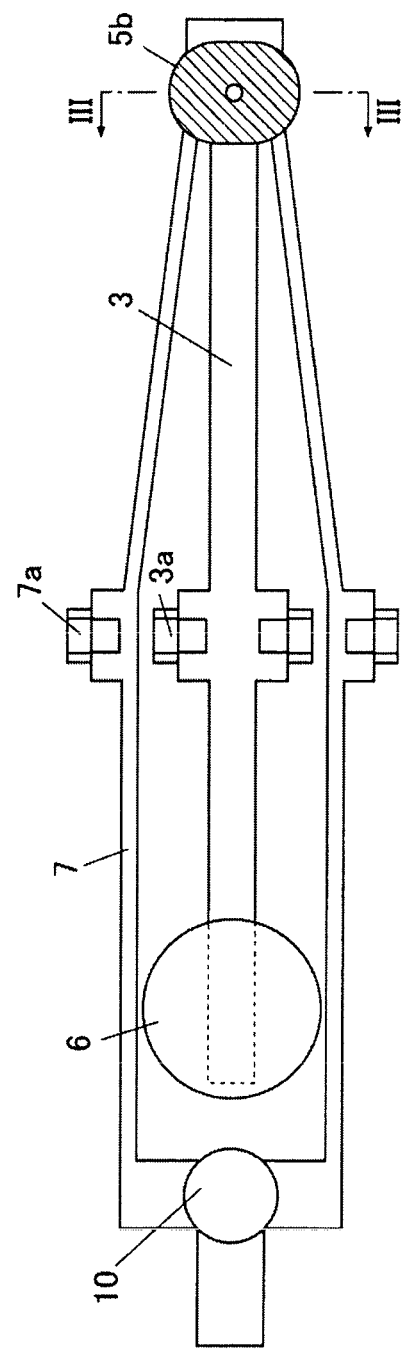
FIG. 2 is a top view illustrating a lever portion of the indentation tester according to the first embodiment.

The reference lever 7 is rotatably and axially supported by a rotation axis 7a, which shares a rotation axis with the load lever 3. The contactor 8 is detachably provided to the lower portion of the first end of the reference lever 7. The second force motor 10 is provided to the upper portion of the second end of the reference lever 7. Moreover, as shown in FIG. 2, when viewed from above, the reference lever 7 has substantially a frame shape and is positioned so as to surround the load lever 3.

The second force motor 10 includes, for example, a force coil 10a and a magnet 10b. Generated power is used as drive power, the power being generated in response to electromagnetic induction between a magnetic field created by the magnet 10b and an electric current flowing through the force coil 10a. The drive power causes the reference lever 7 to rotate, thus pressing down or pressing up the first end of the reference lever 7. The first end of the reference lever 7 is pressed down with the drive from the second force motor 10, causing the contactor 8 to displace in the axis direction of the indenter column 41 and thus enabling the contactor 8 to touch the surface of the sample S. In other words, the second force motor 10 is an indenter reference driver displacing the contactor 8 in the axis direction of the indenter column 41.

The displacement sensor fixed portion 5b is provided to the upper portion of the first end of the reference lever 7 and detects an amount of displacement when the displacement sensor movable portion 5a on the load lever 3 is displaced. In other words, the reference lever 7 is a pressure brace having the contactor 8 attached to the lower portion thereof and the displacement sensor fixed portion 5b on the upper portion thereof.

An indenter displacement sensor 5 is a sensor gauging an amount of movement (displacement) of the indenter 4 using a capacitance method. The indenter displacement sensor 5 includes the displacement sensor movable portion 5a, which is configured with an electrode plate, and the displacement sensor fixed portion 5b, which is configured with a pair of upper and lower electrode plates provided apart from each other with the displacement sensor movable portion 5a therebetween. The indenter displacement sensor 5 gauges the amount of displacement of the indenter 4 based on capacitance between the electrode plates, the capacitance changing in response to a distance between the displacement sensor movable portion 5a and the displacement sensor fixed portion 5b. Specifically, the indenter displacement sensor 5 gauges the displacement of the displacement sensor movable portion 5a with respect to the displacement sensor fixed portion 5b in order to gauge the displacement amount of the indenter 4. Moreover, the indenter displacement sensor 5 outputs to the controller 200 data (a signal) for the gauged amount of displacement of the indenter 4. In addition, the displacement sensor movable portion 5a is fixated to the indenter column 41 and is therefore coupled to the indenter 4. A range for measuring the indentation depth using the indenter displacement sensor 5 is small; however, by using a difference amplifier, sensitivity can be two times greater than when the displacement sensor fixed portion 5b is configured by a single electrode plate. Electric noise and temperature characteristics can also be negated and resolution can therefore be improved. In addition, non-linearity of output voltage can be greatly improved.

Figure 3:
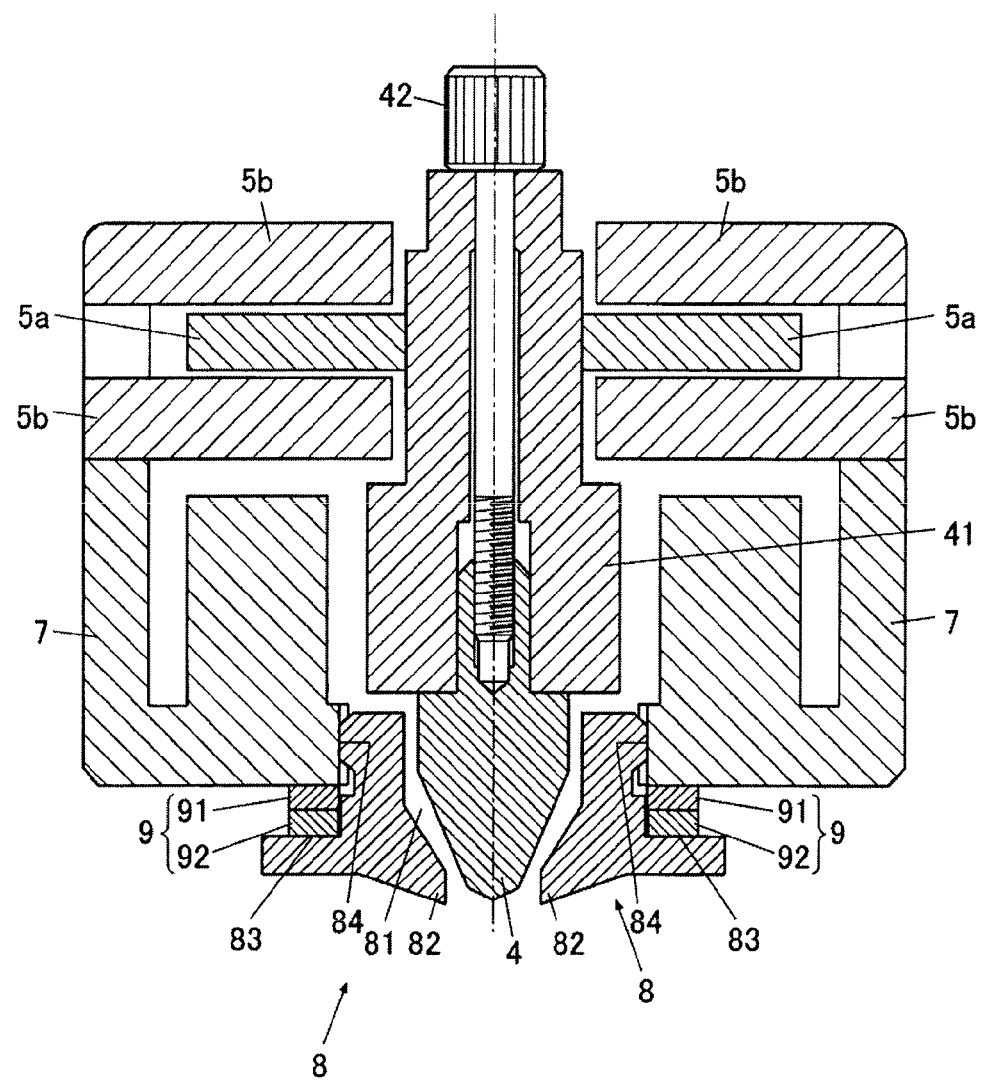
FIG. 3 is a cross-sectional exemplary view along a line in FIG. 2.

As shown in FIG. 3, the contactor 8 is attached to the lower portion of the first end of the reference lever 7 and serves as a vertical-direction positioning reference for the foremost end of the indenter 4, the indenter 4 being provided to the lower portion of the first end of the load lever 3. An aperture 81 is provided in a center portion of the contactor 8, which thus has a round donut shape when viewed from below. The foremost end of the indenter 4 is able to pass through the aperture 81. A downward-projecting sample surface contactor 82 is provided proximate to the aperture 81 on the bottom surface of the contactor 8. The sample surface contactor 82 has a hollow round truncated pyramid shape. The sample surface contactor 82 makes contact with the surface of the sample S, and thus the contactor 8 is the positioning reference for the foremost end of the indenter 4. In addition, a platform 83 on which the adjustment mechanism 9 can be placed is formed on the contactor 8 near an outer circumferential surface thereof (a far side from the indenter 4 in a direction orthogonal to an axis direction of the indenter 4). The adjustment mechanism 9 can thus be held on the platform 83. Furthermore, the contactor 8 is detachably attached to the lower portion of the first end of the reference lever 7 by attachment screws 84 so as to enable the contactor 8 to be removed, e.g., when switching the indenter 4.

Figure 4B:
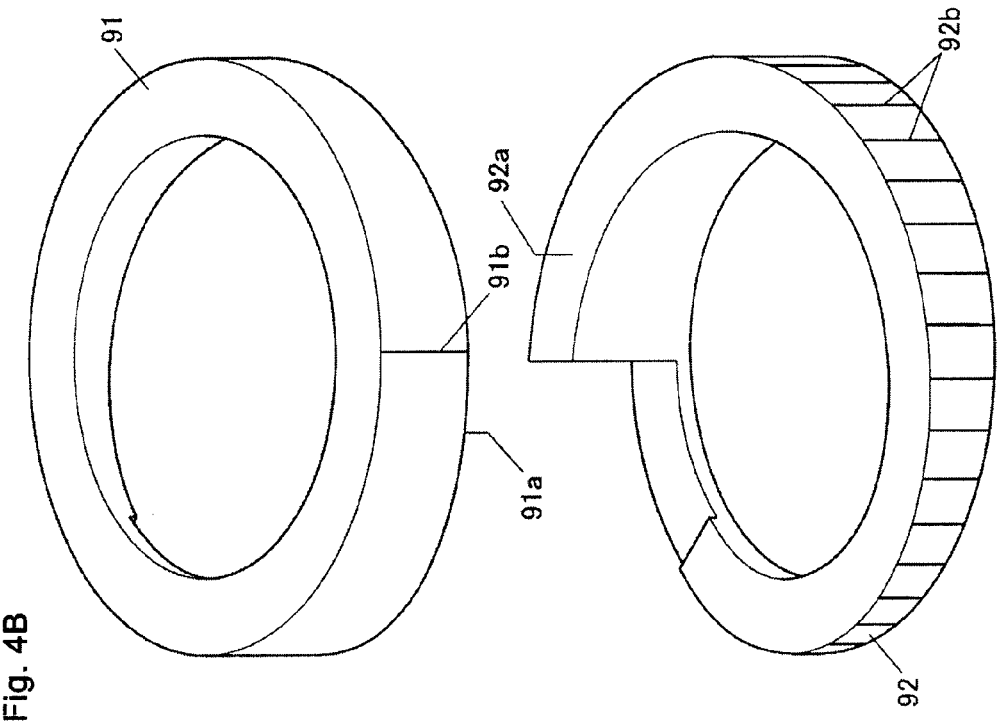
FIGS. 4A and 4B illustrate an adjustment mechanism of the indentation tester according to the first embodiment.
Figure 4A:
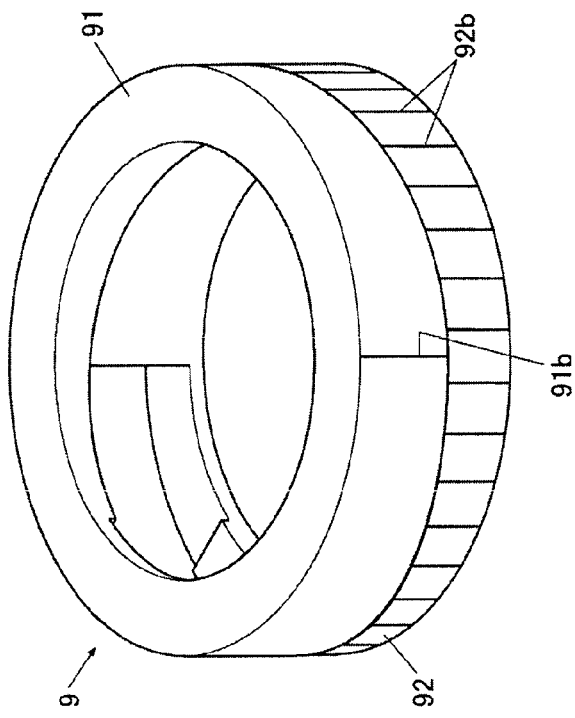

As shown in FIGS. 3 and 4, the adjustment mechanism 9 includes a first hollow disk 91 and a second hollow disk 92, which have a round plate shape with a hollow center. The adjustment mechanism 9 is held atop the platform 83 of the contactor 8 so as to cover the outer circumferential surface of the contactor 8. The first hollow disk 91 and the second hollow disk 92 are formed so as to have identical diameters (inner diameters) and so as to be capable of rotating on the center axis of the indenter column 41. The first hollow disk 91 is placed on a top surface of the second hollow disk 92. A spiraling surface 91a having a narrow thread is formed on a bottom surface of the hollow disk 91. The thread of the spiraling surface 91a of the first hollow disk 91 is, for example, 0.18 mm. An indicator (first indicator) 91b is provided on an outer circumferential surface of the first hollow disk 91 to indicate a rotation-direction position of the first hollow disk 91 when height is minutely adjusted. The top surface of the first hollow disk 91 is further configured so as to contact the bottom surface of the reference lever 7. The second hollow disk 92 is placed on the platform 83 of the contactor 8. A spiraling surface 92a is formed on the top surface of the second hollow disk 92. The thread of the spiraling surface 92a is equal to the thread of the spiraling surface 91a on the first hollow disk 91. Specifically, the spiraling surface 91a of the first hollow disk 91 and the spiraling surface 92a of the second hollow disk 92 are configured so as to mate when stacked. In addition, a plurality of indicators (second indicators) 92b shaped as calibration marks are provided at equal intervals on an outer circumferential surface of the second hollow disk 92 to indicate an amount of change in the height of the adjustment mechanism 9 when the height is minutely adjusted.

As described above, the adjustment mechanism 9 is configured such that the top surface of the first hollow disk 91 contacts the bottom surface of the reference lever 7 and the bottom surface of the second hollow disk 92 contacts the platform 83 of the contactor 8. By rotating the first hollow disk 91 or the second hollow disk 92 on the center axis of the indenter column 41 and offsetting the relative rotation-direction positions of the first hollow disk 91 and the second hollow disk 92, the height of the adjustment mechanism 9 can be minutely adjusted. In addition, the displacement sensor fixed portion 5b can be vertically displaced by minute adjustments to the height of the adjustment mechanism 9 being transferred through the reference lever 7. Accordingly, the adjustment mechanism 9 enables adjustment of the relative vertical-direction positions of the displacement sensor movable portion 5a and the displacement sensor fixed portion 5b such that the displacement sensor movable portion 5a is positioned at a vertical-direction central position (baseline position) of the displacement sensor fixed portion 5b.

The stopper 12 contacts the top surface on the second end of the reference lever 7 so as to regulate the baseline position of the reference lever 7. The stopper 12 is configured with, for example, a micrometer head, the height of which can be adjusted by turning a feed screw. Specifically, by adjusting the height of the stopper 12, a rotation angle of the reference lever 7 (which is in contact with the stopper 12) can be adjusted. Adjustments can also be made such that the stopper 12 does not contact the reference lever 7.

Figure 5:
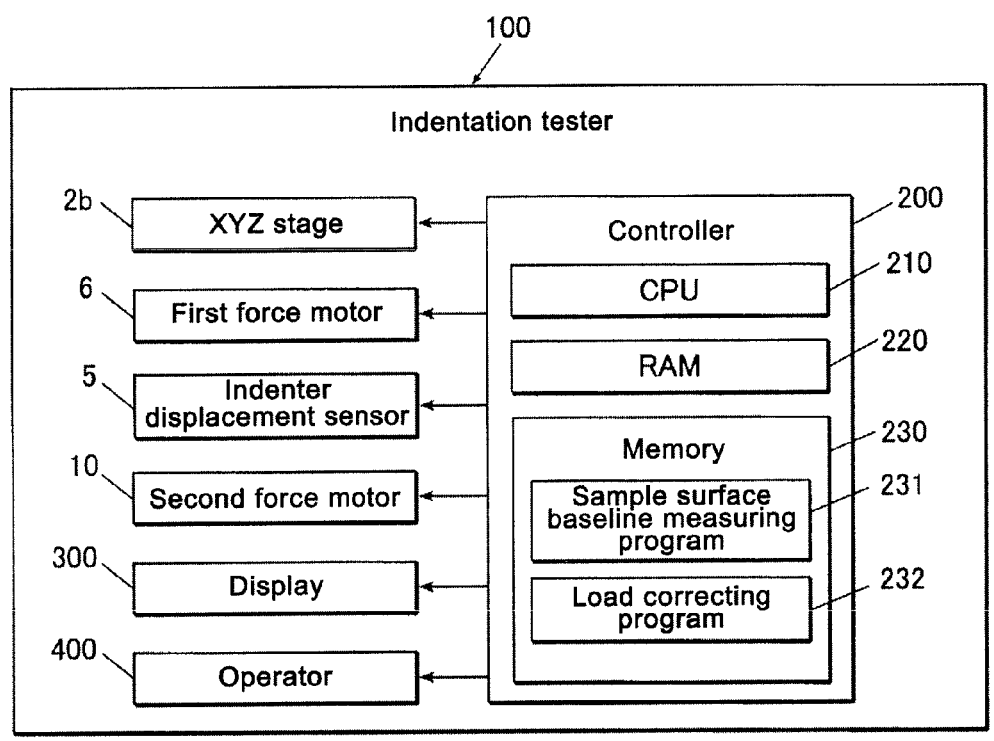
FIG. 5 is a block diagram illustrating essential components of the indentation tester according to the first embodiment.

As shown in FIG. 5, the controller 200 includes a CPU 210, a RAM 220, and a memory 230. The controller 200 is connected, through a system bus, to the XYZ stage 2b, the indenter displacement sensor 5, the first force motor 6, the second force motor 10, the display 300, and the operator 400, for example.

The CPU 210 performs various control processes, for example, in accordance with processing programs for executing various features of the indentation tester 100. The processing programs are stored in the memory 230.

The RAM 220 includes, for example, program storage regions for opening the processing programs executed by the CPU 210 and data storage regions for storing input data or processing results generated when executing the processing programs.

The memory 230 stores, for example, a system program capable of being executed by the indentation tester 100; various processing programs capable of being executed by the system program; data used when executing the various processing programs; and data for results of the various processes, calculated by the CPU 210. Moreover, the programs are stored in the memory 230 in the form of a programming code capable of being read by a computer. Specifically, the memory 230 stores a sample surface baseline measuring program 231, a load correcting program 232, and the like.

The sample surface baseline measuring program 231 is a program executed by the CPU 210 to rotate the load lever 3 starting from a state where the contactor 8 and the foremost end of the indenter 4 are in contact with the sample surface, then measure the indentation depth left by the indenter 4 pressing against the sample S. The measurement is conducted by detecting the amount of change in the capacitance between the displacement sensor fixed portion 5b and the displacement sensor movable portion 5a. In other words, the CPU 210 executes the sample surface baseline measuring program 231, thereby driving the first force motor 6 to rotate the load lever 3, to which the indenter 4 is provided. The depth of the indentation left in the sample S by the indenter 4 is measured by detecting the amount of displacement of the indenter 4, which is gauged by the indenter displacement sensor 5. This provides a measurer. Specifically, starting from a state where the stopper 12 has been adjusted to a position away from the reference lever 7 and the contactor 8 is in contact with the sample S, the indenter 4 is pressed against the sample S, then the indentation depth is measured.

The load correcting program 232 is a program executed by the CPU 210 to regulate the load pressing the contactor 8 against the sample S to a constant load while the CPU 210 (as the measurer) measures the indentation depth. In other words, the CPU 210 executes the load correcting program 232, thereby adjusting the output of the second force motor 10. This regulates the drive on the reference lever 7 and regulates the load pressing the contactor 8 against the sample S to a constant load. Specifically, the CPU 210 is a pressing force when the reference lever 7 presses the contactor 8 down. In order to have the load pressing the contactor 8 against the sample S be constant, the CPU 210 regulates the drive on the reference lever 7 and regulates the load pressing the contactor 8 against the sample S to a constant load.

The display 300 is, for example, a liquid crystal display panel. The display 300 performs processes to display various display screens for test results and the like according to a display signal input from the controller 200.

The operator 400 is, for example, a group of operation keys such as a keyboard. When operated by a worker, the operator 400 outputs to the controller 200 an operation signal corresponding to the operation. The operator 400 may also include a pointing device (such as a mouse or touch screen), a remote control, or some other operation device as needed. In addition, the operator 400 is operated, for example, when the worker inputs a command to perform an indentation test on the sample S.

Next, an operation of switching the indenter 4 in the indentation tester 100 according to the first embodiment is described. First, the worker loosens the attachment screws 84 and removes the contactor 8 from the reference lever 7. Next, after loosening the indenter fixating screw 42 and removing the indenter 4 from the indenter column 41, the worker attaches the new indenter 4 to the indenter column 41 and tightens the indenter fixating screw 42. Next, the worker attaches the contactor 8 to the reference lever 7 and gently tightens the attachment screws 84. Next, based on the indicator 91b on the first hollow disk 91 and the indicators 92b on the second hollow disk 92, the worker rotates the first hollow disk 91 or the second hollow disk 92 in the rotation direction so as to match the relative rotation-direction positions of the first hollow disk 91 and the second hollow disk 92 with the relative positions thereof prior to switching the indenter 4. Next, the worker tightens the attachment screws 84 and firmly affixes the contactor 8 to the reference lever 7. Next, the worker operates the operator 400 to input a command to lower the contactor 8 to a position where the contactor 8 touches the sample S. When the CPU 210 receives the operation signal corresponding to the input command from the operator 400, the CPU 210 controls the second force motor 10 to rotate the reference lever 7 and lower the contactor 8 to touch the sample S. Next, the worker operates the operator 400 to input a command to lower the indenter 4 to a position where the indenter 4 touches the sample S. When the CPU 210 receives the operation signal corresponding to the input command from the operator 400, the CPU 210 controls the first force motor 6 to rotate the load lever 3 and lower the indenter 4 to touch the sample S. Next, the CPU 210 calculates an amount of vertical-direction offset between the baseline position and the relative position of the displacement sensor movable portion 5a with respect to the displacement sensor fixed portion 5b (currently positioned at the sample surface). Herein, the baseline position refers to a position where the displacement sensor movable portion 5a is positioned precisely in a center of the displacement sensor fixed portion 5b (configured by the pair of upper and lower electrode plates) in a state where the contactor 8 and the indenter 4 touch the sample S. Next, the worker loosens the attachment screws 84 and loosens the attachment of the contactor 8. Next, the amount of height offset for each calibration mark is calculated from the threads of the spiraling surfaces 91a and 92a on the first hollow disk 91 and the second hollow disk 92, respectively, and from the number of calibration marks on the indicators 92b on the second hollow disk 92. Then, based on the calculated amount of height offset for each calibration mark, the worker calculates the scale (amount of calibration) corresponding to the amount of vertical-direction offset from the baseline position, then rotates the first hollow disk 91 or the second hollow disk 92 in the rotation direction by the calculated amount of calibration. Finally, the worker tightens the attachment screws 84 and firmly affixes the contactor 8 to the reference lever 7.

As described above, the indentation tester 100 according to the first embodiment includes the adjustment mechanism 9 adjusting the relative vertical-direction positions of the displacement sensor movable portion 5a and the displacement sensor fixed portion 5b. The adjustment mechanism 9 includes the first hollow disk 91 and the second hollow disk 92. The spiraling surface 91a is formed on the bottom surface of the first hollow disk 91. The spiraling surface 92a is formed on the top surface of the second hollow disk 92, the spiraling surface 92a having a thread equal to that of the spiraling surface 91a on the first hollow disk 91. The first hollow disk 91 is placed on the second hollow disk 92 such that the bottom surface of the first hollow disk 91 is overlaid on the top surface of the second hollow disk 92. In addition, the first hollow disk 91 and the second hollow disk 92 are capable of rotating on the center axis of the indenter column 41. Therefore, when the indenter 4 reaches a position at the sample surface, adjustments can be readily made so as to position the displacement sensor movable portion 5a in a vertical-direction central position of the displacement sensor fixed portion 5b (baseline position). In addition, adjustments can be readily and cheaply made to vertical-direction positioning drift that occurs when switching indenters due to individual differences in the indenter 4.

In particular, the indentation tester 100 according to the first embodiment includes the platform 83 formed near the outer circumferential surface of the contactor 8, where the adjustment mechanism 9 can be placed. The top surface of the first hollow disk 91 contacts the bottom surface of the reference lever 7 and the bottom surface of the second hollow disk 92 contacts the platform 83 of the contactor 8. Therefore, the position of the displacement sensor fixed portion 5b can be readily adjusted simply by rotating the first hollow disk 91 or the second hollow disk 92. In addition, adjustments can be readily and cheaply made to vertical-direction positioning drift that occurs when switching indenters due to individual differences in the indenter 4.

Further, the indentation tester 100 according to the first embodiment includes the indicator 91b on the outer circumferential surface of the first hollow disk 91 to indicate the rotation-direction position of the first hollow disk 91 and the indicators 92b on the outer circumferential surface of the second hollow disk 92 to indicate the amount of change in the height of the adjustment mechanism 9. Therefore, by referring to the indicator 91b and the indicators 92b, the height of the displacement sensor fixed portion 5b can be readily adjusted. In addition, adjustments can be even more readily made to vertical-direction positioning drift that occurs when switching indenters due to individual differences in the indenter 4.

Second Embodiment

The second embodiment differs from the first embodiment in that the second embodiment applies the present invention to an indentation tester 110, which is a direct instrumented indentation tester, instead of to the indentation tester 100, which is a lever-type instrumented indentation tester. Specifically, the indentation tester 110 of the second embodiment is a direct instrumented indentation tester capable of continuously monitoring the test force (load) applied to the indenter 4 and the indentation depth for the indenter 4. Moreover, in order to simplify the description, configurations similar to those of the first embodiment are given the same reference numerals and a detailed description thereof is omitted.

Figure 6:
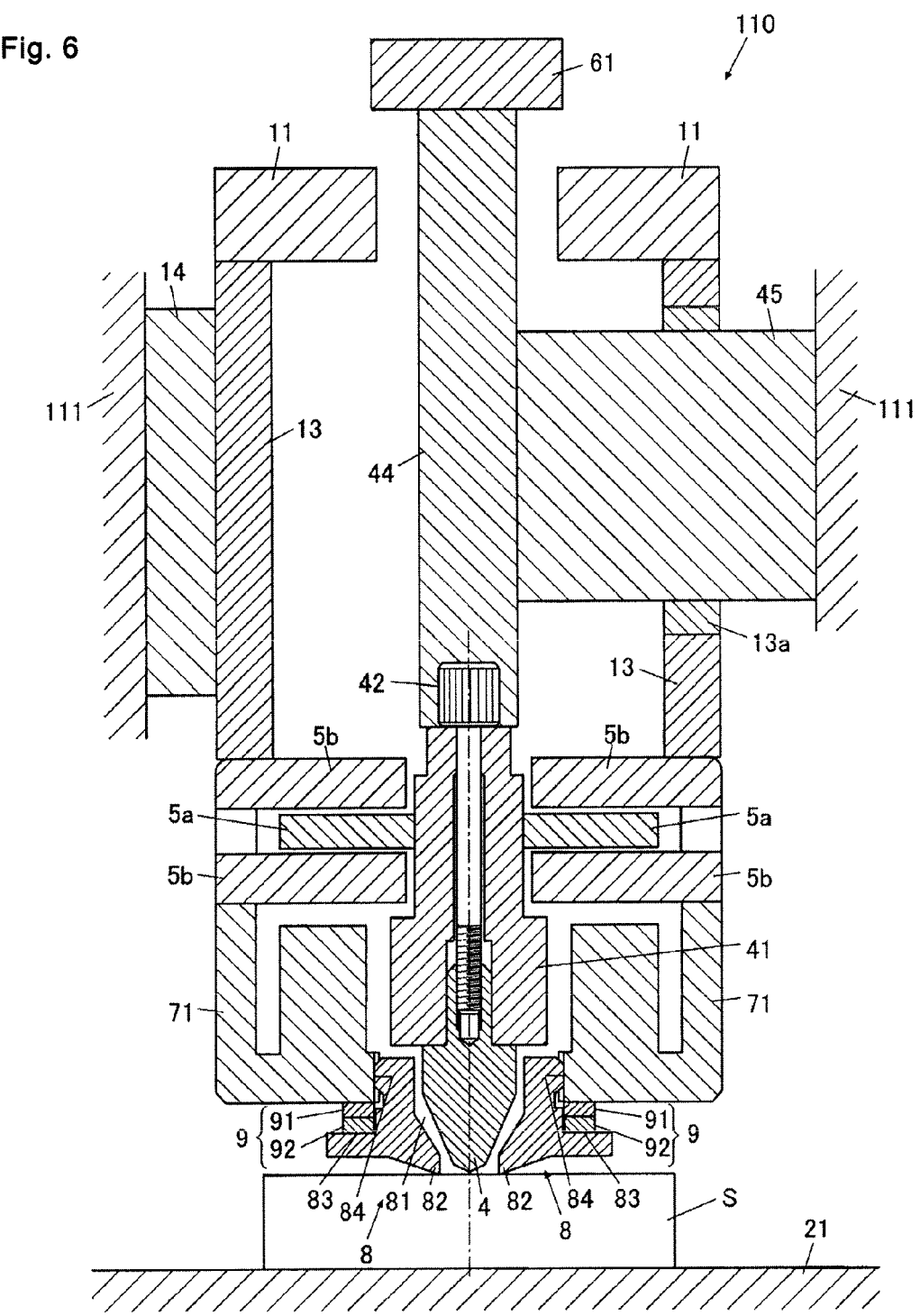
FIG. 6 is a cross-sectional side view of an essential portion of an indentation tester according to a second embodiment of the present invention.
Figure 7:
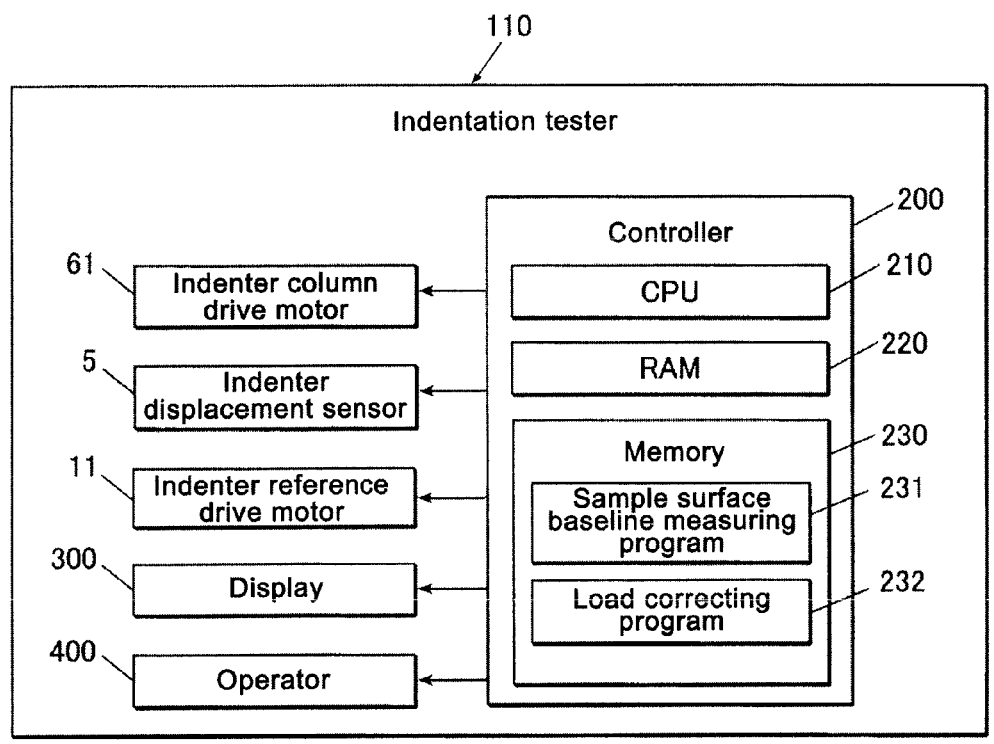
FIG. 7 is a block diagram illustrating essential components of the indentation tester according to the second embodiment.

As shown in FIGS. 6 and 7, the indentation tester 110 includes, for example: a sample stage 21 on which the sample S is placed; the indenter column 41; a displacement sensor movable portion 5a (indenter coupling); a first load transmitter 44; an indenter column guide 45; and an indenter column drive motor (load-applying mechanism) 61. The indenter column 41 holds the indenter 4 on the foremost end of the indenter column 41. The displacement sensor movable portion 5a (indenter coupling) is affixed to the indenter column 41 and has an annular shape when viewed from above. The first load transmitter 44 is affixed to the second end of the indenter column 41. The indenter column guide 45 is affixed at a first end to the first load transmitter 44 and is affixed at a second end to a tester main body 111. The indenter column drive motor (load-applying mechanism) 61 is affixed to a second end of the first load transmitter 44. The indentation tester 110 further includes, for example: a contactor 8 (indenter reference) as a positioning reference for the foremost end of the indenter 4; an adjustment mechanism 9; a displacement sensor fixed portion 5b (indenter position detector) having an annular shape when viewed from above; a pressure brace 71; a second load transmitter 13; an indenter reference guide 14; and an indenter reference drive motor (indenter reference driver) 11. The adjustment mechanism 9 is provided on the outer circumferential surface of the contactor 8. The pressure brace 71 has the contactor 8 attached to a lower portion thereof and the displacement sensor fixed portion 5b on the upper portion thereof. The second load transmitter 13 is affixed to the top surface of the displacement sensor fixed portion 5b and has an annular shape when viewed from above. The indenter reference guide 14 is affixed at a first end to the second load transmitter 13 and affixed at a second end to the tester main body 111. The indenter reference drive motor (indenter reference driver) 11 is affixed to a second end of the second load transmitter 13 and has an annular shape when viewed from above. In addition, the indentation tester 110 includes the controller 200 controlling various components of the indentation tester 110, the display 300, and the operator 400. Moreover, the controller 200 is connected, through the system bus, to the indenter displacement sensor 5, the indenter column drive motor 61, the indenter reference drive motor 11, the display 300, and the operator 400, for example.

The indenter column guide 45 is configured with a blade spring, for example. A first end of the indenter column guide 45 is affixed to the first load transmitter 44, while a second end of the indenter column guide 45 is affixed to the tester main body 111. When a load is applied to the first load transmitter 44, the indenter column guide 45 is configured to bend such that the first load transmitter 44 is pressed down toward the sample stage 21 accompanying application of the load. Moreover, the indenter column guide 45 is inserted through an insertion channel 13a formed on the second load transmitter 13, the second load transmitter 13 being interposed between the first load transmitter 44 and the tester main body 111.

The indenter column drive motor 61 is configured with a force coil and a magnet, for example. Generated power is used as drive power, the power being generated in response to electromagnetic induction between a magnetic field created by the magnet and an electric current flowing through the force coil. The drive power, through the first load transmitter 44, causes the indenter column 41 to be displaced in the axis direction. The indenter column 41 is then pressed down with the drive from the indenter column drive motor 61. A load can thus be applied to the indenter 4 and the indenter 4 can be pressed against the surface of the sample S. In other words, the indenter column drive motor 61 is a load-applying mechanism displacing the indenter column 41 in the axis direction to apply a pre-determined test force to the sample S using the indenter 4.

The contactor 8 is detachably attached to the lower portion of the pressure brace 71. In addition, the displacement sensor fixed portion 5b, which detects the amount of displacement of the displacement sensor movable portion 5a, is provided to the upper portion of the pressure brace 71. In other words, the pressure brace 71 is a pressure brace attached at the lower portion to the contactor 8 and having at the upper portion the displacement sensor fixed portion 5b.

The indenter reference guide 14 is configured with a blade spring, for example. The first end of the indenter reference guide 14 is affixed to the second load transmitter 13 and the second end of the indenter reference guide 14 is affixed to the tester main body 111. When a load is placed on the second load transmitter 13, the indenter reference guide 14 is configured to bend such that the second load transmitter 13 is pressed down toward the sample stage 21 accompanying application of the load.

The indenter reference drive motor 11 is configured with a force coil and a magnet, for example. Generated power is used as drive power, the power being generated in response to electromagnetic induction between a magnetic field created by the magnet and an electric current flowing through the force coil. Thus, the displacement sensor fixed portion 5b and the pressure brace 71 are displaced downward using the second load transmitter 13. Therefore, the contactor 8 can be displaced in the axis direction to touch the surface of the sample S by pressing down the pressure brace 71 with the drive from the indenter reference drive motor 11. In other words, the indenter reference drive motor 11 is an indenter reference driver displacing the contactor 8 in the axis direction of the indenter column 41.

Next, an operation of switching the indenter 4 in the indentation tester 110 according to the second embodiment is described. First, the worker loosens the attachment screws 84 and removes the contactor 8 from the pressure brace 71. Next, after loosening the indenter fixating screw 42 and removing the indenter 4 from the indenter column 41, the worker attaches the new indenter 4 to the indenter column 41 and tightens the indenter fixating screw 42. Next, the worker attaches the contactor 8 to the pressure brace 71 and gently tightens the attachment screws 84. Next, based on the indicator 91b on the first hollow disk 91 and the indicators 92b on the second hollow disk 92, the worker rotates the first hollow disk 91 or the second hollow disk 92 in the rotation direction so as to match the relative rotation-direction positions of the first hollow disk 91 and the second hollow disk 92 with the relative positions thereof prior to switching the indenter 4. Next, the worker tightens the attachment screws 84 and firmly affixes the contactor 8 to the pressure brace 71. Next, the worker operates the operator 400 to input a command to lower the contactor 8 to a position where the contactor 8 touches the sample S. When the CPU 210 receives the operation signal corresponding to the input command from the operator 400, the CPU 210 controls the indenter reference drive motor 11 to lower the pressure brace 71 and lower the contactor 8 to touch the sample S. Next, the worker operates the operator 400 to input a command to lower the indenter 4 to a position where the indenter 4 touches the sample S. When the CPU 210 receives the operation signal corresponding to the input command from the operator 400, the CPU 210 controls the indenter column drive motor 61 to lower the indenter column 41 and lower the indenter 4 to touch the sample S. Next, the CPU 210 calculates an amount of vertical-direction offset between the baseline position and the relative position of the displacement sensor movable portion 5a with respect to the displacement sensor fixed portion 5b (currently positioned at the sample surface). Herein, the baseline position refers to a position where the displacement sensor movable portion 5a is positioned precisely in a center of the displacement sensor fixed portion 5b (configured by the pair of upper and lower electrode plates) in a state where the contactor 8 and the indenter 4 touch the sample S. Next, the worker loosens the attachment screws 84 and loosens the attachment of the contactor 8. Next, the amount of height offset for each calibration mark is calculated from the threads of the spiraling surfaces 91a and 92a on the first hollow disk 91 and the second hollow disk 92, respectively, and from the number of calibration marks on the indicators 92b on the second hollow disk 92. Then, based on the calculated amount of height offset for each calibration mark, the worker calculates the scale (amount of calibration) corresponding to the amount of vertical-direction offset from the baseline position, then rotates the first hollow disk 91 or the second hollow disk 92 in the rotation direction by the calculated amount of calibration. Finally, the worker tightens the attachment screws 84 and firmly affixes the contactor 8 to the pressure brace 71.

As described above, similar to the indentation tester 100 according to the first embodiment, the indentation tester 110 according to the second embodiment includes the adjustment mechanism 9 adjusting the relative vertical-direction positions of the displacement sensor movable portion 5a and the displacement sensor fixed portion 5b. The adjustment mechanism 9 includes the first hollow disk 91 and the second hollow disk 92. The spiraling surface 91a is formed on the bottom surface of the first hollow disk 91. The spiraling surface 92a is formed on the top surface of the second hollow disk 92, the spiraling surface 92a having a thread equal to that of the spiraling surface 91a on the first hollow disk 91. The first hollow disk 91 is placed on the second hollow disk 92 such that the bottom surface of the first hollow disk 91 is overlaid on the top surface of the second hollow disk 92. In addition, the first hollow disk 91 and the second hollow disk 92 are capable of rotating on the center axis of the indenter column 41. Therefore, when the indenter 4 reaches a position at the sample surface, adjustments can be readily made so as to position the displacement sensor movable portion 5a in a vertical-direction central position of the displacement sensor fixed portion 5b (baseline position). In addition, adjustments can be readily and cheaply made to vertical-direction positioning drift that occurs when switching indenters due to individual differences in the indenter 4.

In particular, the indentation tester 110 according to the second embodiment includes the platform 83 formed near the outer circumferential surface of the contactor 8, where the adjustment mechanism 9 can be placed. The top surface of the first hollow disk 91 contacts the bottom surface of the pressure brace 71 and the bottom surface of the second hollow disk 92 contacts the platform 83 of the contactor 8. Therefore, the position of the displacement sensor fixed portion 5b can be readily adjusted simply by rotating the first hollow disk 91 or the second hollow disk 92. In addition, adjustments can be readily and cheaply made to vertical-direction positioning drift that occurs when switching indenters due to individual differences in the indenter 4.

Further, the indentation tester 110 according to the second embodiment includes the indicator 91b on the outer circumferential surface of the first hollow disk 91 to indicate the rotation-direction position of the first hollow disk 91 and the indicators 92b on the outer circumferential surface of the second hollow disk 92 to indicate the amount of change in height of the adjustment mechanism 9. Therefore, by referring to the indicator 91b and the indicators 92b, the height of the displacement sensor fixed portion 5b can be readily adjusted. In addition, adjustments can be even more readily made to vertical-direction positioning drift that occurs when switching indenters due to individual differences in the indenter 4.

A concrete description has been given above with reference to embodiments of the present invention. However, the present invention is not limited to the above-described embodiments and may be modified within the scope of the present invention.

Alternate Example 1

Figure 8:
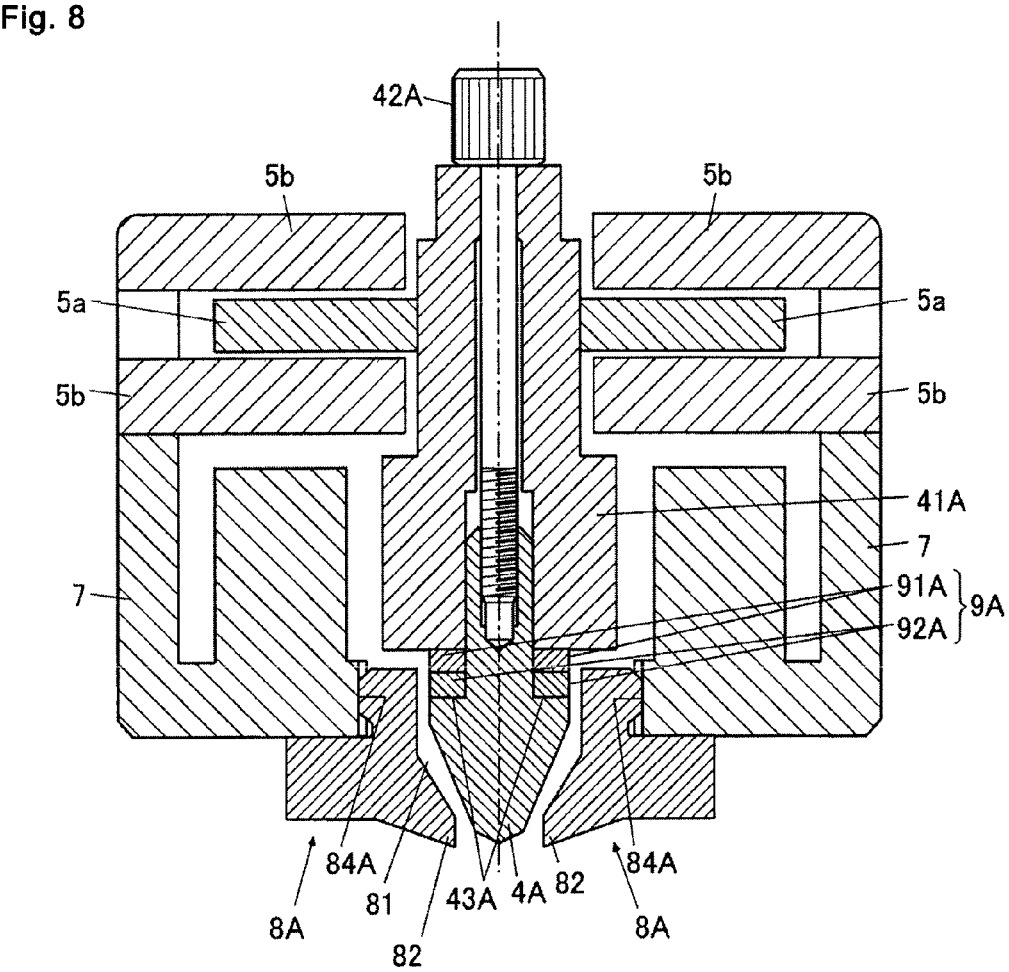
FIG. 8 is a cross-sectional view of an alternate example of the indentation tester shown in FIG. 3.

An example shown in FIG. 8 differs from the first embodiment in the shape of an indenter 4A, the shape of a contactor 8A, and an attachment position of an adjustment mechanism 9A, for example. Specifically, the indenter 4A has a platform 43A on which the adjustment mechanism 9A can be placed, the platform 43A being formed near an outer circumferential surface of a portion of the indenter 4A in contact with a bottom surface of an indenter column 41A. The indenter 4A thus enables the adjustment mechanism 9A to be placed and held on the platform 43A. In Alternate Example 1, a second hollow disk 91B is placed on the platform 43A of the indenter 4A and a top surface of a first hollow disk 91A is in contact with a bottom surface of the indenter column 41A. Specifically, Alternate Example 1 enables the adjustment mechanism 9A to be held by the indenter 4A rather than the contactor 8A.

As described above, the adjustment mechanism 9A is configured such that the top surface of the first hollow disk 91A contacts the bottom surface of the indenter column 41A and a bottom surface of the second hollow disk 91B contacts the platform 43A of the indenter 4A. By rotating the first hollow disk 91A or the second hollow disk 92A about the center axis of the indenter column 41A and offsetting the relative rotation-direction positions of the first hollow disk 91A and the second hollow disk 92A, the height of the adjustment mechanism 9A can be minutely adjusted. In addition, the displacement sensor movable portion 5a can be vertically displaced by minute adjustments to the height of the adjustment mechanism 9A being transferred through the indenter column 41A. Accordingly, the adjustment mechanism 9A enables adjusting the relative vertical-direction positions of the displacement sensor movable portion 5a and the displacement sensor fixed portion 5b so as to position the displacement sensor movable portion 5a in a vertical-direction central position of the displacement sensor fixed portion 5b (baseline position).

In Alternate Example 1, the contactor 8A does not hold the adjustment mechanism 9A and thus the platform 83 is not provided. However, Alternate Example 1 is not limited to this, and the contactor 8 of the first embodiment may be used as described in the first embodiment.

Next, an operation of switching the indenter 4A in the indentation tester 100 according to Alternate Example 1 is described. First, the worker loosens the attachment screws 84A and removes the contactor 8A from the reference lever 7. Next, after loosening the indenter fixating screw 42A and removing the indenter 4A from the indenter column 41A, the worker attaches the new indenter 4A to the indenter column 41A and gently tightens the indenter fixating screw 42A. Next, based on the indicator 91b on the first hollow disk 91A and the indicators 92b on the second hollow disk 92A. Next, the worker tightens the indenter fixating screw 42A and firmly 92A in the rotation direction so as to match the relative rotation-direction positions of the first hollow disk 91A and the second hollow disk 92A with the relative positions thereof prior to switching the indenter 4A. Next, the worker tightens the indenter fixating screw 42A and firmly affixes the indenter 4A to the indenter column 41A. Next, the worker attaches the contactor 8A to the reference lever 7 and tightens the attachment screws 84A. Next, the worker operates the operator 400 to input a command to lower the contactor 8A to a position where the contactor 8A touches the sample S. When the CPU 210 receives the operation signal corresponding to the input command from the operator 400, the CPU 210 controls the second force motor 10 to rotate the reference lever 7 and lower the contactor 8A to touch the sample S. Next, the worker operates the operator 400 to input a command to lower the indenter 4A to a position where the indenter 4A touches the sample S. When the CPU 210 receives the operation signal corresponding to the input command from the operator 400, the CPU 210 controls the first force motor 6 to rotate the load lever 3 and lower the indenter 4A to touch the sample S. Next, the CPU 210 calculates an amount of vertical-direction offset between the baseline position and the relative position of the displacement sensor movable portion 5a with respect to the displacement sensor fixed portion 5b (currently positioned at the sample surface). Herein, the baseline position refers to a position where the displacement sensor movable portion 5a is positioned precisely in a center of the displacement sensor fixed portion 5b (configured by the pair of upper and lower electrode plates) in a state where the contactor 8A and the indenter 4A touch the sample S. Next, the worker loosens the attachment screws 84A and removes the contactor 8A from the reference lever 7. Next, the worker loosens the indenter fixating screw 42A and loosens the attachment of the indenter 4A. Next, the amount of height offset for each calibration mark is calculated from the threads of the spiraling surfaces 91a and 92a on the first hollow disk 91A and the second hollow disk 92A, respectively, and from the number of calibration marks on the indicators 92b on the second hollow disk 92A. Then, based on the calculated amount of height offset for each calibration mark, the worker calculates the scale corresponding to the amount of vertical-direction offset from the baseline position, then rotates the first hollow disk 91A or the second hollow disk 92A in the rotation direction by the calculated scale. Next, the worker tightens the indenter fixating screw 42A and firmly affixes the indenter 4A to the indenter column 41A. Finally, the worker attaches the contactor 8A to the reference lever 7 and tightens the attachment screws 84A.

As described above, the indentation tester 100 according to Alternate Example 1 includes the platform 43A on which the adjustment mechanism 9A can be placed, the platform 43A being formed near the outer circumferential surface of the portion of the indenter 4A in contact with the bottom surface of the indenter column 41A. The top surface of the first hollow disk 91A is in contact with the bottom surface of the indenter column 41A and the bottom surface of the second hollow disk 92A is in contact with the platform 43A of the indenter 4A. Therefore, the position of the displacement sensor movable portion 5a can be readily adjusted simply by rotating the first hollow disk 91A or the second hollow disk 92A. In addition, adjustments can be readily and cheaply made to vertical-direction positioning drift that occurs when switching indenters due to individual differences in the indenter 4A. Moreover, Alternate Example 1 can, of course, also be applied to the indentation tester 110 according to the second embodiment.

Alternate Example 2

Figure 9:
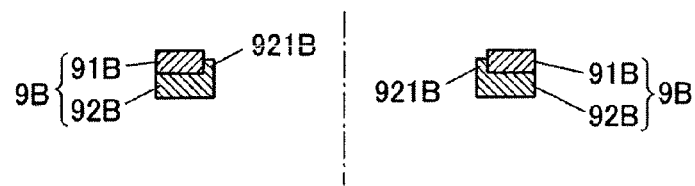
FIG. 9 is a cross-sectional view of an alternate example of an adjustment mechanism.

An example shown in FIG. 9 differs from the first and second embodiments in the shape of an adjustment mechanism 9B. Specifically, a second hollow disk 92B in the adjustment mechanism 9B includes a guide portion 921B on a diametrically interior side, the guide portion 921B projecting upward and guiding rotation of a first hollow disk 91B. In Alternate Example 2, the guide portion 921B is provided on the diametrically interior side; however, the guide portion 921B is not limited to this and may instead be provided on a diametrically exterior side. In addition, in Alternate Example 2, the guide portion 921B is provided to the second hollow disk 92B; however, a guide portion is not limited to this. Instead of being provided to the second hollow disk 92B, a guide portion can be provided on the diametrically interior or exterior side of the first hollow disk 91B, the guide portion projecting downward and guiding rotation of the second hollow disk 92B. Moreover, Alternate Example 2 may also be used in combination with Alternate Example 1.

In the above-described way, the indentation tester 100 according to Alternate Example 2 includes the guide portion provided to one of the first hollow disk 91B and the second hollow disk 92B, the guide portion guiding rotation of the other hollow disk. Therefore, when the first hollow disk 91B or the second hollow disk 92B is rotated, the hollow disk can be operated in a stable way, without tilting the contactor 8 or the indenter 4A holding the hollow disk. In addition, adjustments can be readily and cheaply made to vertical-direction positioning drift that occurs when switching indenters due to individual differences in the indenter.

Additional Alternate Examples

In the first and second embodiments, the indicator (first indicator) 91b is provided on the outer circumferential surface of the first hollow disk 91 to indicate a rotation-direction position of the first hollow disk 91. In addition, the indicators (second indicators) 92b are provided on the outer circumferential surface of the second hollow disk 92 to indicate an amount of change in the height of the adjustment mechanism 9. However, the indicators are not limited to this and instead indicators indicating the amount of change in the height of the adjustment mechanism 9 may be provided on the outer circumferential surface of the first hollow disk 91 while an indicator indicating the rotation-direction position of the second hollow disk 92 may be provided on the outer circumferential surface of the second hollow disk 92.

Figure 10:
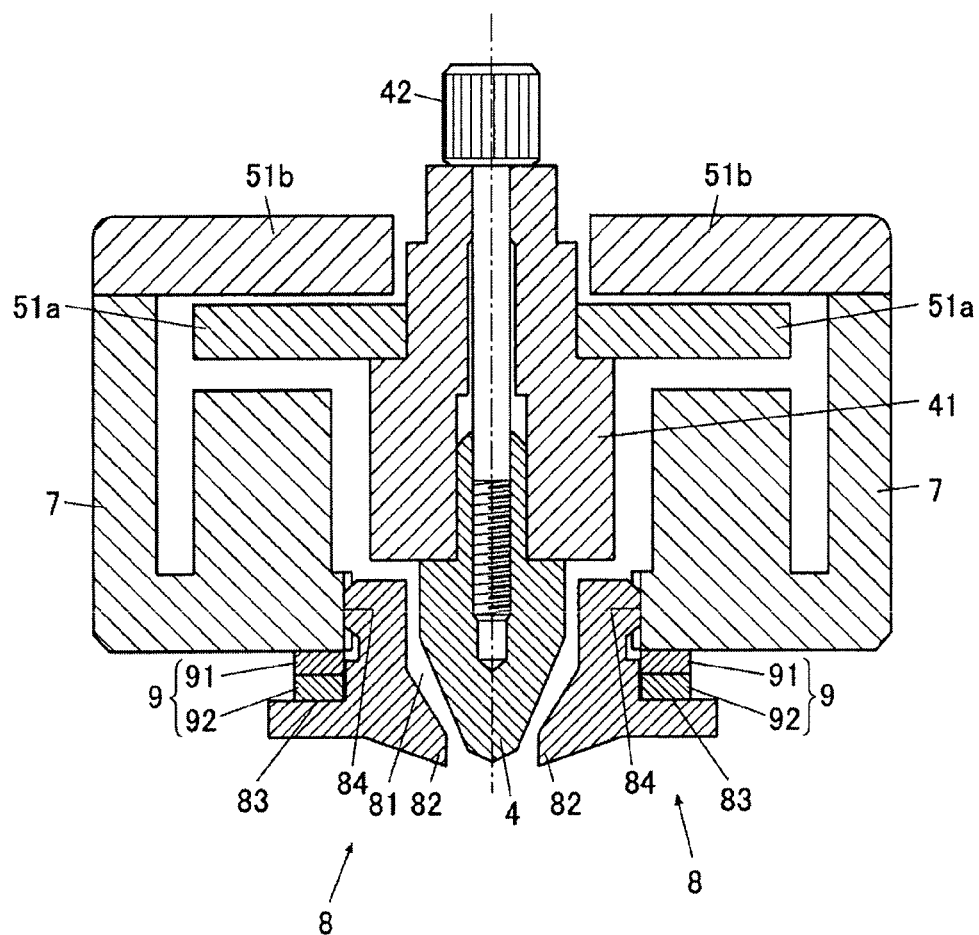
FIG. 10 is a cross-sectional view of an alternate example of an indenter displacement sensor in the indentation tester shown in FIG. 3.

In the first and second embodiments, a configuration of the indenter displacement sensor 5 includes the displacement sensor movable portion 5a and the displacement sensor fixed portion 5b. The displacement sensor fixed portion 5b includes a pair of upper and lower electrode plates provided apart from each other with the displacement sensor movable portion 5a therebetween. However, the indenter displacement sensor is not limited to this. As shown in FIG. 10, for example, an indenter displacement sensor 51 may instead include a displacement sensor movable portion 51a configured with an electrode plate and a displacement sensor fixed portion 51b configured with a single electrode plate positioned above the displacement sensor movable portion 51a. The indenter displacement sensor 51 enables a measurement of the indentation depth to be taken over a broader range and thus enables a wide variety of values for physical characteristics of the sample S to be measured.

Additionally, appropriate modifications not departing from the scope of the present invention may be made in details of configuration and operation of each component included in the indentation tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. An indentation tester comprising:
    an indenter column holding an indenter on a foremost end of the indenter column;
    an indenter coupling affixed to the indenter column and coupled with the indenter;
    a load-applier configured to displace the indenter column in an axial direction of the indenter column and further configured to apply a predetermined test force to a sample using the indenter;
    an indenter reference configured to reference a position of a foremost end of the indenter;
    an indenter position detector coupled to the indenter reference and configured to detect an amount of displacement of the indenter coupling;
    a pressure brace, wherein the indenter reference is attached to a lower portion of the pressure brace, and wherein the indenter position detector is attached to an upper portion of the pressure brace;
    an indenter reference driver configured to displace the indenter reference in the axial direction of the indenter column; and
    a measurer configured to displace the indenter column in the axial direction while maintaining contact between the indenter reference and a surface of the sample, the measurer further configured to thereafter measure a depth of an indentation formed when the indenter, while in contact with the sample surface, was pressed against the sample, wherein the indenter position detector is configured to measure the indentation depth by detecting the displacement amount of the indenter coupling;
    an adjuster configured to adjust a relative vertical-direction position relationship between the indenter coupling and the indenter position detector, the adjuster comprising:
        a first hollow disk having a first spiral formed on a bottom surface thereof; and
        a second hollow disk having a second spiral formed on a top surface thereof, the second spiral having threading equal to that of the first spiral, wherein:
            the first hollow disk rests on the second hollow disk such that the bottom surface of the first hollow disk overlays on the top surface of the second hollow disk, and
            the first hollow disk and the second hollow disk are configured to rotate about a center axis of the indenter column.

2. The indentation tester according to claim 1, wherein:
the indenter reference comprises a platform on an outer circumferential surface of the indenter reference, the platform configured to accept placement of the adjuster thereon,
a top surface of the first hollow disk is in contact with a bottom surface of the pressure brace, and
a bottom surface of the second hollow disk is in contact with the platform of the indenter reference.

3. The indentation tester according to claim 2, wherein one of the first hollow disk and the second hollow disk comprises a guide configured to guide rotation of the other of the first hollow disk and the second hollow disk.

4. The indentation tester according to claim 3, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

5. The indentation tester according to claim 2, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

6. The indentation tester according to claim 1, further comprising a platform configured to accept placement of the adjuster thereon, the platform formed proximate an outer circumferential surface of a portion of the indenter in contact with a bottom surface of the indenter column, wherein:
a top surface of the first hollow disk is in contact with the bottom surface of the indenter column, and
a bottom surface of the second hollow disk is in contact with the platform of the indenter.

7. The indentation tester according to claim 6, wherein one of the first hollow disk and the second hollow disk comprises a guide configured to guide rotation of the other of the first hollow disk and the second hollow disk.

8. The indentation tester according to claim 7, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

9. The indentation tester according to claim 6, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

10. The indentation tester according to claim 1, wherein one of the first hollow disk and the second hollow disk comprises a guide configured to guide rotation of the other of the first hollow disk and the second hollow disk.

11. The indentation tester according to claim 10, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

12. The indentation tester according to claim 1, wherein:
an outer circumferential surface of one of the first hollow disk and the second hollow disk comprises a first indicator configured to indicate a rotation-direction position of the hollow disk, and
an outer circumferential surface of the other of the first hollow disk and the second hollow disk comprises a second indicator configured to indicate an amount of change in height of the adjuster.

* * * * *